United States Patent [19]
Bast et al.

[11] Patent Number: 5,164,920
[45] Date of Patent: Nov. 17, 1992

[54] COMPOSITE ULTRASOUND TRANSDUCER AND METHOD FOR MANUFACTURING A STRUCTURED COMPONENT THEREFOR OF PIEZOELECTRIC CERAMIC

[75] Inventors: Ulrich Bast, Munich; Hans Kaarmann, Buckenhof; Karl Lubitz, Ottobrunn; Martina Vogt, Fuerth; Wolfram Wersing, Kirchheim; Dieter Cramer, Holzkirchen, all of Fed. Rep. of Germany

[73] Assignee: Siemens Aktiengesellschaft, Munich, Fed. Rep. of Germany

[21] Appl. No.: 706,354

[22] Filed: May 28, 1991

[30] Foreign Application Priority Data

Jun. 21, 1990 [EP] European Pat. Off. .......... 90111796

[51] Int. Cl.⁵ ............................................. H04R 17/00
[52] U.S. Cl. ...................................... 367/140; 367/155; 367/157; 310/322; 310/334; 128/24 AA; 128/662.03
[58] Field of Search ............... 367/153, 155, 157, 140; 310/322, 334; 128/660.01, 662.03, 24 AA

[56] References Cited

U.S. PATENT DOCUMENTS

| | | | |
|---|---|---|---|
| 4,156,158 | 5/1979 | Wilson et al. | 310/369 |
| 4,305,014 | 12/1981 | Borburgh et al. | 310/334 |
| 4,398,116 | 8/1983 | Lewis | 310/334 |
| 4,398,325 | 8/1983 | Piaget et al. | 310/334 |
| 4,617,707 | 10/1986 | Mohaupt et al. | 29/25.35 |
| 4,658,176 | 4/1987 | Nakaya et al. | 310/334 |
| 4,801,835 | 1/1989 | Nakaya et al. | 310/334 |
| 4,963,782 | 10/1990 | Bui et al. | 310/358 |
| 5,045,746 | 9/1991 | Wersing et al. | 310/334 |

FOREIGN PATENT DOCUMENTS

| | | |
|---|---|---|
| 3437862 | 5/1985 | Fed. Rep. of Germany . |
| 3739226 | 6/1989 | Fed. Rep. of Germany . |
| 2114856 | 8/1983 | United Kingdom . |

OTHER PUBLICATIONS

"Fabrication of microstructures with high aspect rations and great structual heights by synchrotron radiation lithography, galvanoforming, and plastic moulding (LIGA process)", E. W. Becker et al. Microelectronic Engineering 4 (1986) pp. 35–56.

Primary Examiner—J. Woodrow Eldred
Attorney, Agent, or Firm—Hill, Van Santen, Steadman & Simpson

[57] ABSTRACT

A composite ultrasound transducer (array) contains piezoelectric ceramic transducer elements which radiate substantially in the longitudinal direction, and are embedded in a polymer matrix. The transducer elements have such a geometrical structure, and are arranged relative to each other, so that the development of oscillation modes perpendicular to the longitudinal direction of the transducer elements is suppressed. A method for manufacturing the composite ultrasound transducer includes the steps of filling a plastic form, having a "negative" of the desired shape of the transducer elements, with ceramic slurry, and pyrolyzing the plastic form after the slurry dries therein. The resulting voids between the hardened ceramic elements are filled with polymer to create the overall composite transducer. The transducer elements can thus be given an arbitrary shape and arrangement, such as hexagonal or irregular square structures, having a trapezoidal cross-section in planes parallel to the longitudinal axis of the transducer elements.

12 Claims, 3 Drawing Sheets

COMPOSITE ULTRASOUND TRANSDUCER AND METHOD FOR MANUFACTURING A STRUCTURED COMPONENT THEREFOR OF PIEZOELECTRIC CERAMIC

BACKGROUND OF THE INVENTION

1. Field of the Invention

The present invention relates to a composite ultrasound transducer, also known as a transducer array, with piezoelectric transducer elements therein radiating substantially in their longitudinal direction. A method for manufacturing such a composite transducer, having at least one structured piezoelectric ceramic transducer element therein, is also disclosed.

1. Description of the Prior Art

Composite ultrasound transducers, also known as transducer arrays, are used in medical diagnostics. A composite ultrasound transducer consists of many small piezoelectrically active, individual transducer elements. The dimensions of the transducer elements are selected so that they radiate substantially in the longitudinal direction, i.e., in a direction along the "thickness" dimension of the transducer elements and of the transducer array. The transducer elements are contained in a plastic matrix, so that the respective longitudinal axes of the transducer elements are parallel to each other. The thickness of the individual transducer elements (i.e., their length along the longitudinal axis) determines the thickness of the composite ultrasound transducer.

Known composite ultrasound transducers are a form of a structured transducer. Structured ultrasound transducers have many advantages compared to unstructured transducers. In a structured transducer, the division of the overall transducer into individual transducer elements results in the suppression of low-frequency cross modes of oscillation, which can result in image artifacts in the resulting ultrasound image. The structuring results in a reduction in "jamming" of the transducer elements. Consequently, the coupling factor, the piezo-module, and thus the sound intensity of the composite ultrasound transducer increases in the thickness direction, and these factors approach the higher values of a bar oscillating in the longitudinal direction. The individual transducer elements can be electrically driven in groups by correspondingly divided electrodes. By doing so, the direction or focusing of the ultrasound signal is electrically variable. This can be used to advantage in phased-array transducers or annular-array transducers.

It is known that the properties of the composite ultrasound transducer depend on the form, size and arrangement of the individual transducer elements.

A composite ultrasound transducer is disclosed in German OS 34 37 862, wherein square prisms consisting of piezoelectric ceramic are embedded as transducer elements in a regular, linear arrangement in a polymer matrix. The manufacture of such a composite ultrasound transducer is undertaken by a method known as the dice-and-fill technique. In this technique, a sintered ceramic disk is divided into prisms by cross and transverse sawing. The saw kerfs have a depth which is less than the thickness of the ceramic disk, so that an uncut ceramic base or backing remains. The kerfs are filled with plastic, and the ceramic base is then ground away.

This manufacturing technique imposes restrictions and limitations on the geometry and arrangement of the individual elements of the ultrasound transducer. The fineness which can be achieved by the kerfs is limited to the thickness of the saw blade. Thus, the manufacture of ultrasound transducers with operating frequencies larger than 7.5 Mhz is possible only in limited fashion. Due to the sawing, only straight cuts with vertical edges can be generated. Therefore, the side faces of the individual transducer elements structured by sawing are parallel. It is known, however, that parallel side faces of the transducer elements favor the development of undesired cross modes of oscillation. Since the kerfs are straight cuts which proceed across the entire ceramic disk, only regular arrangements with intolerably large distances between the individual transducer elements can be generated. These large distances result in a reduction of the portion of the ceramic surface which is active for ultrasound generation.

Moreover, the precision sawing needed in the above technique is very time-consuming. The risk of damage, such as breakage of the ceramic disk, during the sawing is particularly high in the case of fine structures, as are necessary for making composite ultrasound transducers with high operating frequencies.

SUMMARY OF THE INVENTION

It is an object of the present invention to provide a composite ultrasound transducer having improved suppression of cross modes of oscillation, by means of the geometry of the transducer.

Another object of the present invention is to provide a manufacturing method for such a composite ultrasound transducer which does not impose restrictions in the design of the transducer.

The above objects are achieved in accordance with the principles of the present invention in a composite ultrasound transducer, and method for making such a transducer, having transducer elements radiating substantially in their longitudinal direction and consisting of piezoelectric ceramic, with the transducer elements being contained in a plastic matrix in a plane perpendicular to their longitudinal direction, so that intermediate spaces exist between the individual transducer elements which are completely filled with plastic polymer. The transducer elements have a geometrical structure and are arranged relative to each other so that a the development of oscillation modes perpendicular to the longitudinal direction of the transducer elements is suppressed in the overall composite transducer.

Suppression of oscillation modes in the transverse direction can be achieved by providing the transducer elements with a trapezoidal cross-section, as seen in a sectional plane containing the longitudinal axis. Due to the trapezoidal cross-section, the side faces of the transducer elements are not parallel to each other in the longitudinal direction. This means that fewer cross waves can develop. Furthermore, the trapezoidal cross-section reduces the risk of mechanical cross-talk between adjacent transducer elements.

It is also within the framework of the invention to arrange the transducer elements in irregular, nonlinear fashion. A random or a fluctuating size distribution of the transducer elements is thus possible. Given a fluctuating size distribution the composite ultrasound transducer is divided into regions or sections, with all of the transducer elements contained within one region being of equal size, and the transducer elements in other regions being of random sizes. Compared to regular, rectangular grid arrangements, the development of unwanted oscillation modes in the transverse direction is thus made more difficult. This embodiment, moreover, has technological advantages, because the risk is reduced that detachment between the transducer elements and the plastic polymer therebetween will occur as a consequence of different expansion coefficients, or during mechanical processing.

If the transducer elements are provided with a hexagonal cross-section in a plane perpendicular to their longitudinal axes, a high packing density of transducer elements is achievable in the composite ultrasound transducer constructed in accordance with the principles of the present invention. The useable transducer area is thus increased.

For the suppression of undesired collective oscillation modes in the composite ultrasound transducer, the transducer elements have cross-sections of random sizes, as seen perpendicular to their longitudinal axes. Cross modes can be suppressed dependent on the geometry of the composite ultrasound transducer by dividing the transducer elements into groups. The transducer elements of each group are contained within a spatially coherent region, and the size of the respective cross-sections of the transducers within that group (the cross-sections as seen perpendicularly to the longitudinal axis) are statistically scattered around a prescribed value for that group with a fluctuation range also prescribed per group.

The use of transducer elements with an aspect ratio (height/width) in the range of from 1.5 to 2.0 is preferable because disturbing oscillation modes in the transverse direction are shifted in a more easily controllable frequency range above the desired frequency, the desired frequency being the resonant frequency in the thickness direction. Moreover, the pulse-echo transmission factor is maximized by this ratio.

The composite transducer having non-regular and non-rectangular transducer elements can be manufactured by the following method. A plastic form is generated which represents a "negative" of a prescribed structure for the individual transducer elements. A ceramic slip or slurry is poured into the form, and the slurry is dried to form the components of piezoelectric ceramic. The form consists of a known type of plastic which pyrolyzes with the application of heat thereto without solid residues, and without modifying the structure of the component which has become fixed during the drying step. The structure of the finished component consisting of piezoelectric ceramic is basically determined by the form. Restrictions regarding the design are therefore only those limitations which are imposed by the possibilities for the generation of the form.

The form may consist of material used in the known LIGA method, as described in Microelectronic Engineering, E. W. Becker et al, Vol. 4, (1986), pages 35 et seq. The structure of the form is defined by depth-sensitive lithography. Therefore any structure can be achieved which can be drawn on paper. Structures with edges having a prescribed inclination to the perpendicular can be generated.

With this technique, forms with structures having arbitrary cross-section and arbitrary element arrangement can be manufactured. The structures can be generated with vertical or oblique edges, depending on the intended application. The restriction on the form and arrangement of the structures is imposed only by the resolution capability of the photolithography technique which is used.

It is preferable to perform the preparation of the ceramic slurry and the filling of the form with the slurry under vacuum, so that gas bubbles in the ceramic slurry and air inclusions in the form are avoided.

The ceramic slip or slurry must be prepared with a binding agent, which does not dissolve the form. It is preferable to use a water-soluble binding agent because, apart from meeting this requirement, such a binding agent has a good firing efficiency, and is environmentally safe.

The method disclosed herein is particularly suitable for manufacturing a composite ultrasound transducer of the type described above. The form is generated so that it represents a negative of the structures corresponding to a prescribed arrangement of the transducer elements, with the border of the form projecting over the negative structures. The form is filled with the ceramic slurry to level exceeding the depth of the negative structures, so that during the drying and baking of the ceramic slurry, a continuous backing or base consisting of piezoelectric ceramic results. The voids which result after the pyrolyzing of the form are filled with material having low mechanical coupling properties, and negligible electrical conductivity. Due to such damping properties, mechanical cross-talk between adjacent transducer elements in the finished composite ultrasound transducer is suppressed. The continuous base or backing is ground away after the voids have been filled.

This method has the advantage that the geometry and arrangement of the transducer elements can be optimized to the intended application of the composite ultrasound transducer. Restrictions regarding the design of the composite ultrasound transducer are present only to the extent of the resolution capability of the lithography technique used for the structuring the original form, and by the necessity of completely filling the negative structures in the form with the ceramic slurry. These restrictions arise, however, only in the case of very small structures, and do not restrict the arrangement and shape of the transducer elements. Tests have shown that structures with a diameter of 5 μm and more can be reliably manufactured using this method.

DESCRIPTION OF THE PREFERRED EMBODIMENTS

Figure 1:
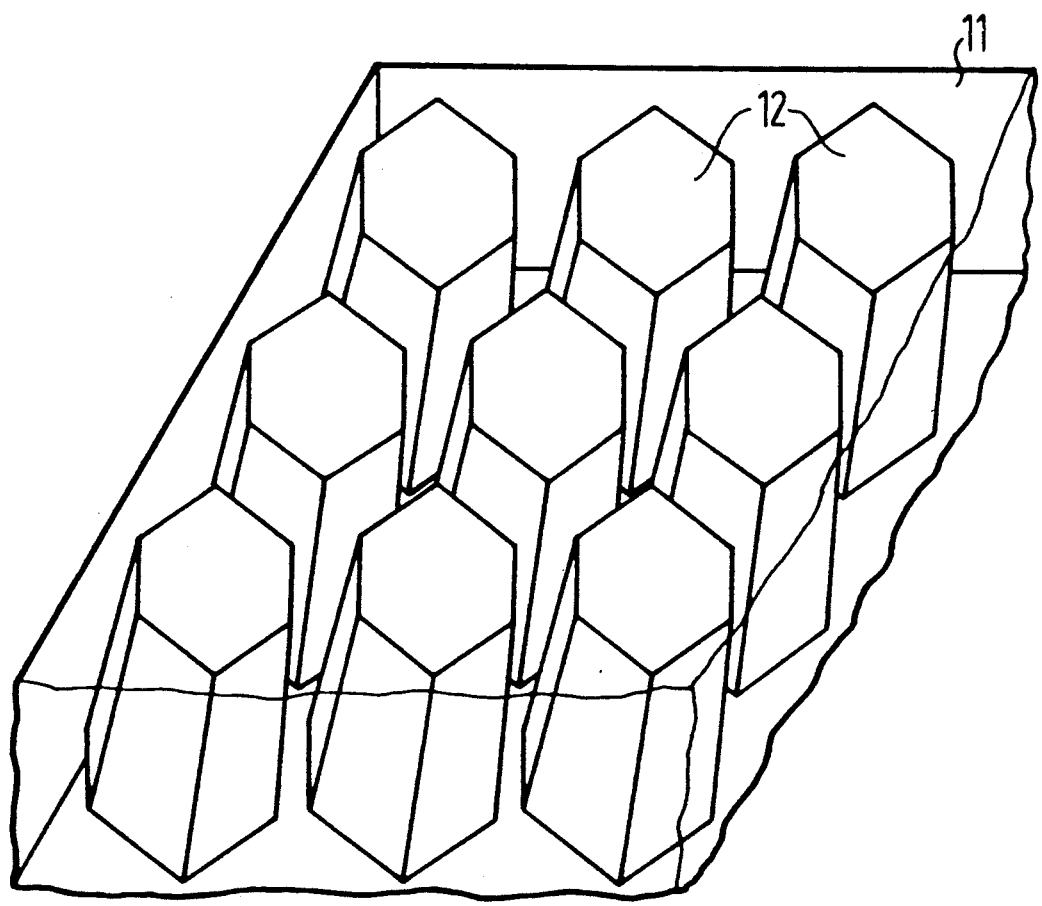
FIG. 1 is a perspective view of a portion of a composite ultrasound transducer constructed in accordance with the principles of the present invention, with the individual transducer elements having a hexagonal cross-section as seen in a plane perpendicular to their longitudinal axes.

A portion of a composite ultrasound transducer constructed in accordance with the principles of the present invention is shown in FIG. 1. The composite transducer has a plurality of individual transducer elements 12 contained in a plastic matrix 11. The plastic matrix 11 consists, for example, of a polymer. The transducer elements 12 consist of piezoelectric ceramic. The transducer elements 12 are arranged so that their longitudinal axes are parallel to each other. The transducer elements 12 have a hexagonal cross-section in a plane perpendicular to their longitudinal axes. The transducer elements 12 are arranged in alveolated fashion, which results in a good utilization of the available area. The transducer elements have a trapezoidal cross-section as seen in plane parallel to their longitudinal axes.

Figure 2:
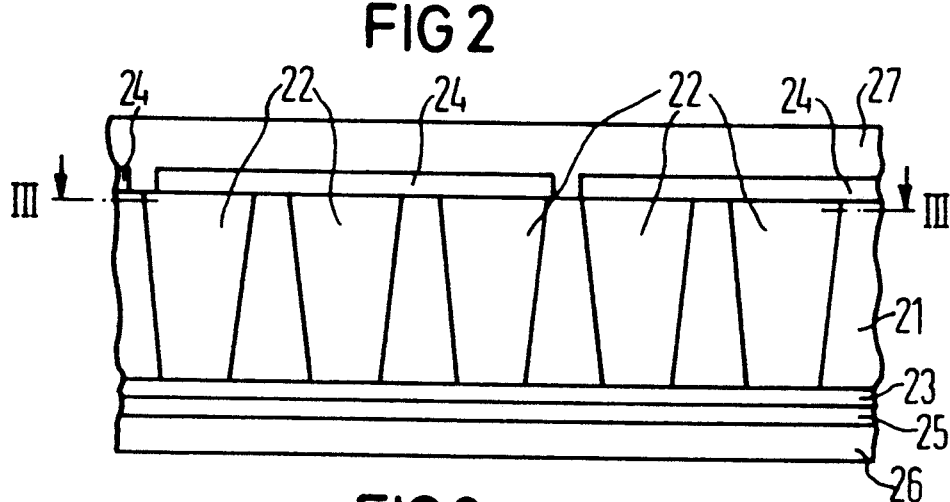
FIG. 2 is a side view of a composite ultrasound transducer having transducer elements with a trapezoidal cross-section, as seen a plane parallel to their longitudinal axes.
Figure 3:
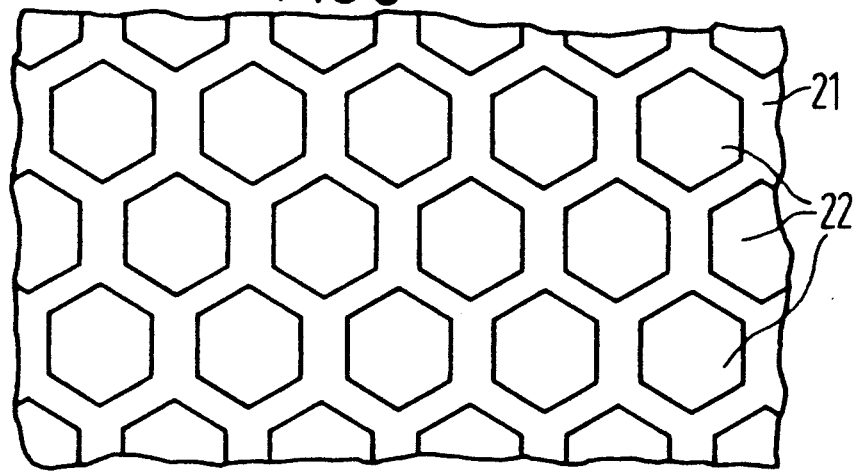
FIG. 3 is a sectional view taken along line III—III of FIG. 2.

A side view as seen through a completed composite ultrasound transducer, parallel to the longitudinal axes of the transducer elements, is shown in FIG. 2. Transducer elements 22 are contained in a plastic matrix 21 so that their longitudinal axes are parallel to each other. The matrix 21 consists of a polymer. The transducer elements 22 consist of piezoelectric ceramic, such as lead zirconate titanate. The transducer elements 22 have a trapezoidal cross-section, as seen in plane parallel to their longitudinal axes. The deviations of the side faces of the transducer elements 22 from the perpendicular are in the range, for example, 1° to 5°. As can be seen in FIG. 3, the base of each transducer element 22 is a hexagon. At the base of the trapezoidal cross-section, the transducer elements 22 have an edge length of, for example, in the range from 25 to 350 µm. The height of the transducer elements 22 is, for example, in the range of 50 to 500 µm. The transducer elements 22 thus have an aspect ratio in the range from 1.5 to 2.0. The distance between adjacent transducer elements 22 at the base of the trapezodial cross-section is, for example, in the range of 1 to 50 µm.

The transducer elements 22 are arranged in the composite ultrasound transducer, for example, so that the narrow side of the trapezoidal cross-section points parallel to the transmission direction for the ultrasound. It is also possible to arrange the transducer elements 22 so that the wide side of the trapezodial cross-section points in the transmission direction. On the surface of the plastic matrix 21 and the transducer elements 22, which faces the transmission direction, a whole-area electrode 23 is disposed. On the opposite surface, a structured electrode 24 is provided. Depending upon the intended application of the composite ultrasound transducer, the structured electrode 24 may be annular or linear. Using the structured electrode 24, predetermined transducer elements 22 are combined into separately driveable groups. The electrodes 23 and 24 may consist, for example, of sputtered CrPtAu.

Over the whole-area electrode 23, one layer, or several sub-layers, are arranged in a known manner forming an acoustic impedance matching layer 25. A focusing lens 26 is arranged over the acoustic impedance matching layer 25. The focusing lens 26 can be omitted if it is not required for the particular application for which the composite ultrasound transducer is intended. A dampling layer 27 is arranged over the structured electrode 24 in a known manner. The damping layer 27 absorbs ultrasound output occurring in a direction opposite to the transmission direction.

Figure 4:
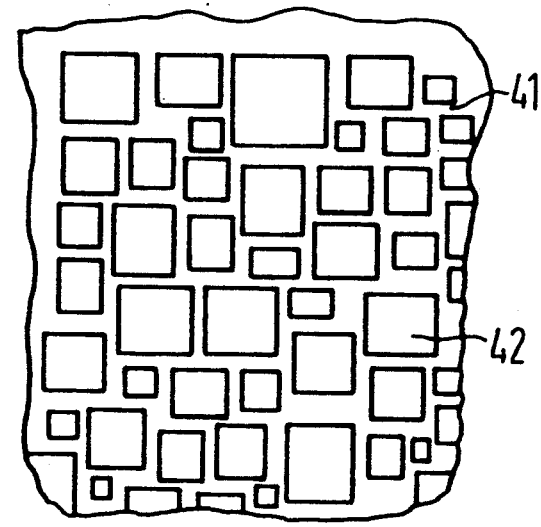
FIG. 4 is a plan view of a further embodiment of a composite ultrasound transducer constructed in accordance with the principles of the present invention having transducer elements with irregular, square cross-sections.

A further embodiment of a composite ultrasound transducer constructed in accordance with the principles of the present invention is shown in FIG. 4, having transducer elements 42. FIG. 4 shows a view taken perpendicularly to the longitudinal axes of the transducer elements 42. Again, the transducer elements 42 are contained in a plastic matrix 41. The transducer elements 42 have square cross-sections of varying sizes. The length of the edges of the individual transducer elements 42 varies within defined limits. The transducer elements 42 are arranged so that, perpendicular to the longitudinal axes of the transducer elements 42, no plastic channels exist which proceed completely across the entire composite ultrasound transducer. As a result of this irregular arrangement of the transducer elements 42, undesired partial oscillations, reaching across several transducer elements 42, are suppressed. The cross-section of the transducer elements 42 parallel to their longitudinal axes can be rectangular, however suppression of cross modes is improved if the cross-section of the transducer elements 42 in this direction is trapezoidal.

Figure 5:
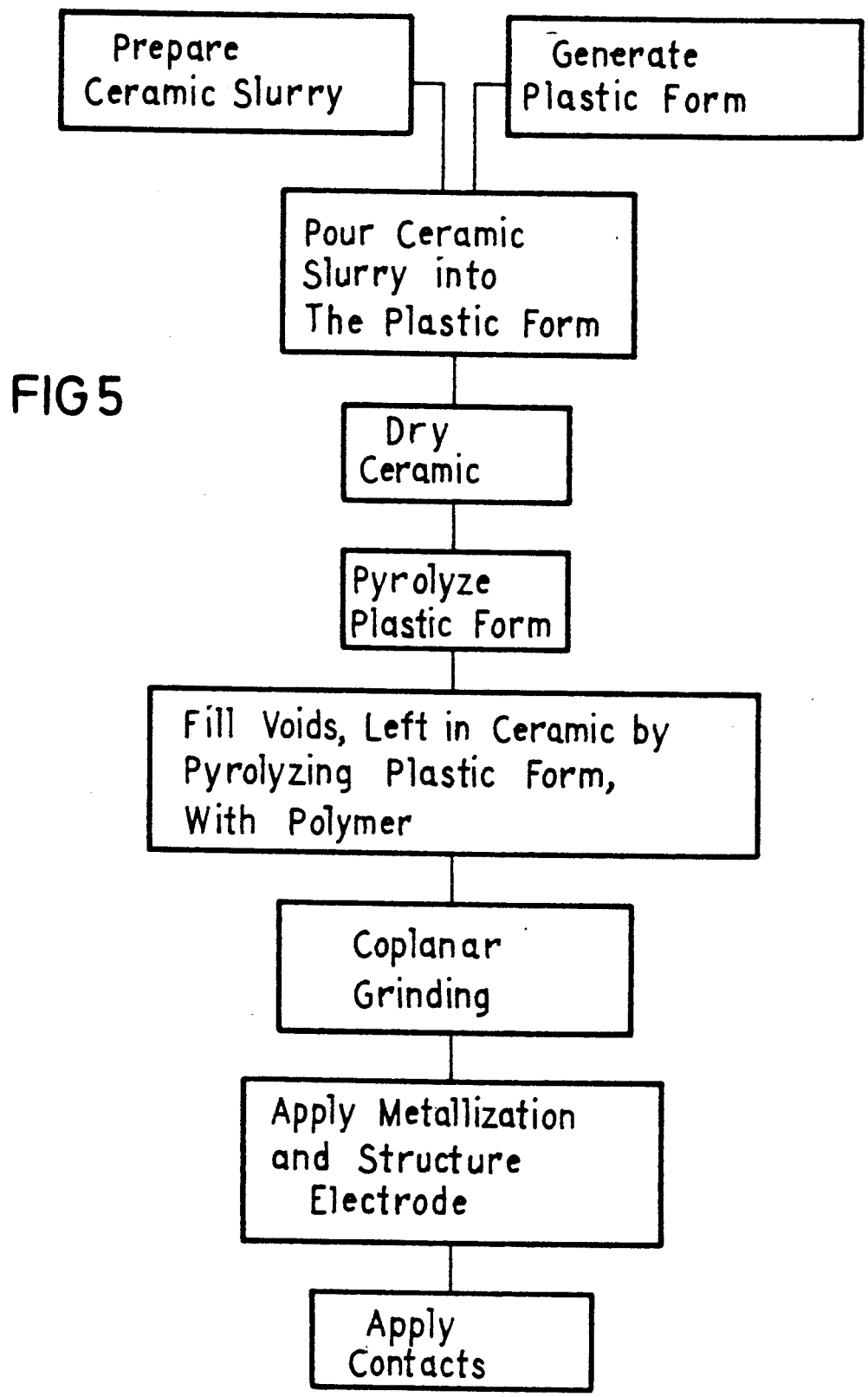
FIG. 5 is a flow chart showing the method steps in the method in accordance with the principles of the present invention.

FIG. 5 is a flow chart showing the steps of a method for manufacturing the various composite ultrasound transducers shown in FIGS. 1 through 4. A detailed example based on FIG. 5 is as follows.

A ceramic slip or slurry is prepared from a conventional ceramic powder, for example, lead zirconate titanate. The slip is poured, under vacuum, into a plastic form having receptacles therein having shapes and dimensions representing a negative of the desired transducer structure. The slip must be prepared with a binding agent which must not dissolve the plastic form. It is therefore preferable to prepare the slip with a water soluble binding agent such as, for example, polyvinyl alcohol. A water soluble binding agent also results in a better fritting efficiency and protection of the environment.

The slip or slurry must also have a viscosity suitable for pouring, while simultaneously having a high density and being free of agglomerates. This is achieved by homogenizing the slurry, such as by grinding the slurry in an attritor mill, and disperging the slurry, such as by placing the slurry in an ultrasound field.

In order to avoid gas bubbles in the slurry, and air inclusions in the form, all steps from the preparation of the binding agent to the filling of the form take place under vacuum.

The structured plastic form is generated by molding using a galvanoplastically-generated "negative" form (i.e., a form which is a "negative" of the intended negative form.) A known technique for manufacturing such a form is the aforementioned LIGA method. The plastic form consists of a reaction resin or from thermoplastic such as, for example, polymethylmethacrylate or polyoxymethylen.

The slurry is filled into the plastic form to a level so that the receptacles of the plastic form are completely covered, and a layer of slurry above the receptacles remains. In the subsequent drying and baking steps, a continuous, unstructured backing or base of piezoelectric ceramic results from this excess layer, which serves as an intermediate carrier, during manufacture, for the transducer elements.

To prevent tears as the ceramic slip dries, it is preferable to perform the drying step under defined temperature and humidity conditions. The ceramic slurry is dried thermally. Because the plastic form does not pyrolyze during the drying, there is a risk that tears could develop in the ceramic. Therefore, the drying step must be performed slowly and uniformly. It is preferable to begin the drying step at a high relative humidity of, for example, 90%, and a low temperature of, for example, 30° C. The humidity is gradually reduced and the temperature is gradually increased, until reaching a point at which the slurry has sufficiently hardened so that it does not ripple.

After drying, the combination of the plastic form and dried ceramic material is subjected to elevated heating (baking). During this step, the plastic form pyrolyes. For pyrolysis of the organic components of the plastic form, it is preferable to conduct this step under temperature and atmospheric conditions matched to the type of plastic comprising the form. For certain plastics it is preferable to perform the pyrolysis step in a pure oxygen atmosphere. In the pyrolysis step, the plastic form burns without solid residues. The plastic comprising the plastic form is selected such that, during the pyrolysis step, the plastic burns without changing (damaging) the dried ceramic structure. The ceramic sinters to a monolithic block having voids therein which are defineed by the structure of the plastic form. These voids are filled with a polymer which fixes the relative positions of the tranducer elements, and which provides mechanical stability for the composite ultrasound transducer while also fulfilling the necessary acoustical requirements. The polymer must be able to accommodate expansions and contractions of the transducer elements in directions transverse to their longitudinal axes. As noted above, the material used to fill the voids should have low mechanical coupling properties, so that a minimum of cross-talk occurs between the transducer elements of the composite ultrasound transducer. For this purpose, epoxide resins and acrylates are particularly suitable. Subsequently, the top and bottom surfaces of the composite transducer are abraded in co-planar fashion, so that parallel surfaces result.

The intermediate structure achieved by the above steps is then subjected to further steps, which are known, for completing the composite ultrasound transducer. On the surface emitting ultrasound, a whole-area electrode is applied. This area will cover a surface perpendicular to the longitudinal axes of the transducer elements. On the opposite side, a structured electrode is applied. The electrodes are generated by sputtering or evaporation of CrPtAu. The structuring of the structured electrode is achieved by conventional photolithographic methods. Over the whole-area electrode, one layer or several sub-layers are applied for matching the acoustical impedance in a known manner, and if required by the intended application, a focusing lens can be provided over the matching layer. The whole-area electrode and the individual elements of the structured electrodes are provided with electrical contacts by soldering or bonding thin wires thereto. A damping layer is then applied on the structured electrode in a known manner.

The method has the advantage that the shape, arrangement and distribution of the individual transducer elements over the surface of the composite ultrasound transducer are determined by a mask production technique. Therefore, non-linear shapes can be used, such as surface-covering hexagons, and intentionally irregular structures can be generated in a simple manner.

The method also permits the generation of defined cross-section by use of depth-sensitive lithography in the generation of the form. Contrary to known manufacturing methods, the cross-section of the transducer elements in a plane parallel to the longitudinal axes thereof is not determined by the limitations of mechanical processing, but is instead determined by the requirements for the finished composite ultrasound transducer. The method is particularly suited for manufacturing a composite transducer having transducer elements with a trapezoidal cross-section.

Because the ceramic is sintered, the walls of the transducer elements will have a so-called sinter skin. Compared to transducer elements which are manufactured using known techniques, such as by sawing, this has the advantage of freedom from mechanical defects and undisturbed piezoelectric properties at the transducer element surface. The roughness of these walls lies in the range of the grain size of the ceramic. This roughness ensures an optimum adhesion of the ceramic to the polymer after casting.

Although the manufacturing method disclosed herein has been described in the context of the exemplary embodiment of the manufacture of a composite ultrasound transducer, it is also suitable for manufacturing other components containing piezoelectric ceramic such as, for example, bending elements and drives. Again, in these other applications, it is an advantage that the geometrical shape of the piezoelectric ceramic components is determined only by the photolithographic method for manufacturing the corresponding plastic form.

Although modifications and changes may be suggested by those skilled in the art, it is the intention of the inventors to embody within the patent warranted hereon all such changes and modifications as reasonably and properly come within the scope of their contribution to the art.

We claim as our invention:

1. A composite ultrasound transducer comprising:
   a plurality of piezoelectric ceramic transducer elements each having lateral sides and each having a longitudinal axis along which the transducer element radiates;
   a polymeric matrix in which said transducer elements are contained in a plane perpendicular to said longitudinal axes with gaps between all transducer elements completely filled with matrix material; and
   said transducer elements each having a geometrical structure and being arranged in said matrix with each transducer having a trapezoidal cross-section in a vertical plane containing said longitudinal axis and with the lateral sides of any adjacent transducer elements being non-parallel for suppressing oscillation modes in a direction perpendicular to said longitudinal axes.

2. A composite ultrasound transducer as claimed in claim 1 wherein all of said transducer elements have the same length along said longitudinal axes, and wherein each transducer element has respective first and second faces disposed in respective further planes which are parallel to said plane, and wherein said composite ultrasound transducer further comprises first and second electrodes respectively electrically contacting said first and second faces.

3. A composite ultrasound transducer as claimed in claim 1 wherein each transducer element has an aspect ratio in range of between 1.5 to 2.0.

4. A composite ultrasound transducer as claimed in claim 1 wherein said transducer elements are arranged in said matrix in an irregular, non-linear fashion so that no channels of matrix material are present extending completely across said composite ultrasound transducer in any further plane which is parallel to said plane perpendicular to said longitudinal axes.

5. A composite ultrasound transducer as claimed in claim 1 wherein each transducer element has lateral faces inclined with respect to said longitudinal axis in the range of from 1° to 5°.

6. A composite ultrasound transducer as claimed in claim 1 wherein each transducer element has a length along said longitudinal axis in the range of from 50 to 500 μm, and wherein each transducer element has a rectangular cross-section at a base of said trapezoidal cross-section having an edge length in the range of from 25 to 350 μm.

7. A composite ultrasound transducer as claimed in claim 1 wherein each transducer element has a length along said longitudinal axis in the range of from 50 to 500 μm, and wherein each transducer element has a hexagonal cross-section at a base of said trapezoidal cross-section having an edge length in the range of from 25 to 350 μm.

8. A composite ultrasound transducer as claimed in claim 1 wherein adjacent transducer elements in said matrix are separated at a base of said trapezoidal cross-section by a distance in the range of from 1 to 50 μm.

9. A composite ultrasound transducer as claimed in claim 1 wherein each transducer element has a hexagonal cross-section in any further plane which is parallel to said plane perpendicular to said longitudinal axes.

10. A composite ultrasound transducer as claimed in claim 1 wherein each transducer element has a rectangular cross-section in any further plane which is parallel to said plane perpendicular to said longitudinal axis.

11. A composite ultrasound transducer as claimed in claim 1 wherein said transducer elements respectively have varying cross-sections in said plane perpendicular to said longitudinal axes.

12. A composite ultrasound transducer comprising:
a plurality of piezoelectric ceramic transducer elements each having a longitudinal axis along which the transducer element radiates;
a polymeric matrix in which said transducer elements are contained in a plane perpendicular to said longitudinal axes with gaps between all transducer elements completely filled with matrix material; and
said transducer elements each having a geometrical structure and having respectively varying cross-sections in said plane perpendicular to said longitudinal axes and being arranged in said matrix in groups, with each transducer element belonging to only one group, the transducer elements of one group being disposed in a spatially continuous region of said matrix and the size of said cross-sections of said transducer elements in said plane in said group being statistically scattered by a predetermined value for that group with a predetermined fluctuation for that group, for suppressing oscillation modes in a direction perpendicular to said longitudinal axes.

* * * * *